(12) United States Patent
Mohiuddin

(10) Patent No.: US 8,057,406 B2
(45) Date of Patent: Nov. 15, 2011

(54) EXTRAVASATION DETECTION DEVICE

(75) Inventor: Khader Mohiuddin, Eden Prairie, MN (US)

(73) Assignee: Acist Medical Systems, Inc., Eden Prairie, MN (US)

( * ) Notice: Subject to any disclaimer, the term of this patent is extended or adjusted under 35 U.S.C. 154(b) by 223 days.

(21) Appl. No.: 12/297,060

(22) PCT Filed: Apr. 17, 2007

(86) PCT No.: PCT/US2007/066751
§ 371 (c)(1),
(2), (4) Date: Jan. 23, 2009

(87) PCT Pub. No.: WO2007/124298
PCT Pub. Date: Nov. 1, 2007

(65) Prior Publication Data
US 2009/0204070 A1 Aug. 13, 2009

Related U.S. Application Data

(60) Provisional application No. 60/745,133, filed on Apr. 19, 2006.

(51) Int. Cl.
*A61B 5/117* (2006.01)
*A61B 5/103* (2006.01)

(52) U.S. Cl. ........................................ 600/587

(58) Field of Classification Search .................. 600/547, 600/587, 561; 604/500; 128/903; 73/718, 73/729.1; 700/9; 711/100
See application file for complete search history.

(56) References Cited

U.S. PATENT DOCUMENTS

| 3,853,118 A | 12/1974 | Schendel |
| 4,122,837 A | 10/1978 | Leonard |
| 4,122,838 A | 10/1978 | Leonard |
| 4,127,110 A * | 11/1978 | Bullara ......................... 600/561 |
| 4,989,615 A | 2/1991 | Hochberg |
| 6,425,878 B1 | 7/2002 | Shekalim |

(Continued)

FOREIGN PATENT DOCUMENTS

DE 2912947 A1 10/1980

(Continued)

OTHER PUBLICATIONS

"PCT International Search Report dated May 8, 2008 for PCT/US2007/066751, from which U.S. Appl. No. 12/297,060 is based," 1 pg.

(Continued)

*Primary Examiner* — Max Hindenburg
*Assistant Examiner* — Brian Szmal
(74) *Attorney, Agent, or Firm* — Fredrikson & Byron, P.A.

(57) ABSTRACT

One embodiment provides an extravasation detection device having an enclosure, an attachment coupled to the enclosure to be removably connected to a patient, and a detection assembly enclosed within the enclosure, in this embodiment, the detection assembly includes a housing and a transducer coupled to the housing to generate a signal representative of a force or pressure applied to the detection device caused by extravasation of medical fluid from the patient. This embodiment of a detection device may be attached to the patient's hand or other injection site. When extravasation occurs, and a swelling or blister presses against the transducer, an alarm can be triggered to warn a clinician, or the device can cause a powered injection system to automatically shut down or halt the injection process.

18 Claims, 8 Drawing Sheets

U.S. PATENT DOCUMENTS 6,461,329 B1   10/2002   Van Antwerp et al.
2007/0260213 A1*  11/2007   Williams et al. .............. 604/500

FOREIGN PATENT DOCUMENTS

WO          0160431  A1    8/2001

OTHER PUBLICATIONS

"PCT Written Opinion dated May 27, 2008 for PCT/US2007/066751, from which U.S. Appl. No. 12/297,060 is based," 3 pgs.
"PCT International Preliminary Report on Patentability dated Oct. 22, 2008, from which U.S. Appl. No. 12,197,060 is based," 4 pgs.
English Translation of First Office Action issued in related Chinese Patent Application No. 200780022041.9 (Apr. 7, 2010), 5 pgs.
English Translation of Second Office Action issued in related Chinese Patent Application No. 200780022041.9 (Apr. 5, 2011), 4 pgs.
European Search Report in related European Patent Application No. 07760749.7 (Mar. 29, 2010), 6 pgs.
Response filed in related European Patent Application No. 07760749.7 (Jan. 13, 2011), 13 pgs.
Supplemental European Search Report in related European Patent Application No. 07760749.7 (Feb. 8, 2011), 5 pgs.
Response filed in related European Patent Application No. 07760749.7 (Jul. 15, 2011), 11 pgs.

* cited by examiner ated into an automated injection system that is coupled to an
EXTRAVASATION DETECTION DEVICE

RELATED APPLICATIONS

This application claims priority to International Application No. PCT/US2007/066751 filed Apr. 17, 2007, and to U.S. Provisional Patent Application No. 60/745,133 filed Apr. 19, 2006, the teachings of which are incorporated herein by reference.

TECHNICAL FIELD

The present application relates generally to the use of an extravasation detection device in medical systems, and more specifically to a device that may be used to detect extravasation of a contrast medium from a patient during a medical injection procedure.

BACKGROUND

In many medical diagnostic and therapeutic procedures, a physician or other trained clinician injects fluid into a patient. For example, during a computed tomography (CT) procedure, a physician may inject a contrast medium into a patient to help improve the visibility of internal bodily structures in one or more X-ray images that are taken during the procedure. To inject the contrast medium, the clinician may use a manual injection syringe, or may alternatively use a powered contrast media injection device. A cannula is coupled to the manual injection syringe or injection device and is used to inject the contrast medium into the patient (such as into a vessel in the patient's hand or arm).

Extravasation is often characterized as an accidental infusion of an injection fluid, such as a contrast medium, into tissue surrounding a blood vessel rather than into the blood vessel itself. Extravasation can be caused, for example, by a fragile vascular system, valve disease, inappropriate needle placement, or patient movement resulting in the infusing needle being pulled from the intended vessel or causing the needle to be pushed through the wall of the vessel. Furthermore, high injection pressures and/or rates of some modern procedures increase the risk of extravasation. In CT, for example, contrast injection flow rates can range, in some cases, from 0.1 to 10 ml/s, which may increase the potential for extravasation.

Complications related to extravasation may potentially be quite severe and may include tissue necrosis. This may require reconstructive surgery to repair. It is, therefore, very important when performing fluid injections to detect extravasation as soon as possible and discontinue the injection upon detection.

Several extravasation detection techniques are known in the art. Two simple and very useful techniques for detecting extravasation are palpation of the patient in the vicinity of the injection site and simple visual observation of the vicinity of the injection site by a clinician. In the palpation technique, the clinician manually senses swelling of tissue near the injection site resulting from extravasation. When using the visual observation technique, it is also sometimes possible to directly observe any swelling of the skin in the vicinity of an injection site resulting from extravasation.

In addition to the palpation and observation techniques, there are a number of automated methods of detecting extravasation. These methods include forms of subcutaneous temperature detection at or near the injection site, microwave extravasation detection, impedance change detection and measurement, optical sensing detection, as well as certain other techniques. Some of these methods provide for an automatic triggering of an alarm condition upon detection of extravasation.

BRIEF SUMMARY

Various embodiments of the present invention provide for a reusable extravasation detection device. In one embodiment, this detection device may be attached to the patient's hand or other injection site. When extravasation begins to occur, a swelling or blister can start to form on the patient near the injection site. As the swelling or blister touches and presses against a sensor on the extravasation detection device, an alarm can be triggered to warn the physician (or technician), or the device can cause a powered injection system to automatically shut down or halt the injection process. In one embodiment, the extravasation detection device comprises a force sensor that is encased in a plastic housing with a sensor load platform that is exposed to atmosphere and enclosed in flexible rubber housing.

One embodiment provides an extravasation detection device having an enclosure, an attachment coupled to the enclosure to be removably connected to a patient, and a detection assembly enclosed within the enclosure. In this embodiment, the detection assembly includes a housing and a transducer coupled to the housing to generate a signal representative of a force or pressure applied to the detection device caused by extravasation of medical fluid from the patient.

DETAILED DESCRIPTION

Figure 1:
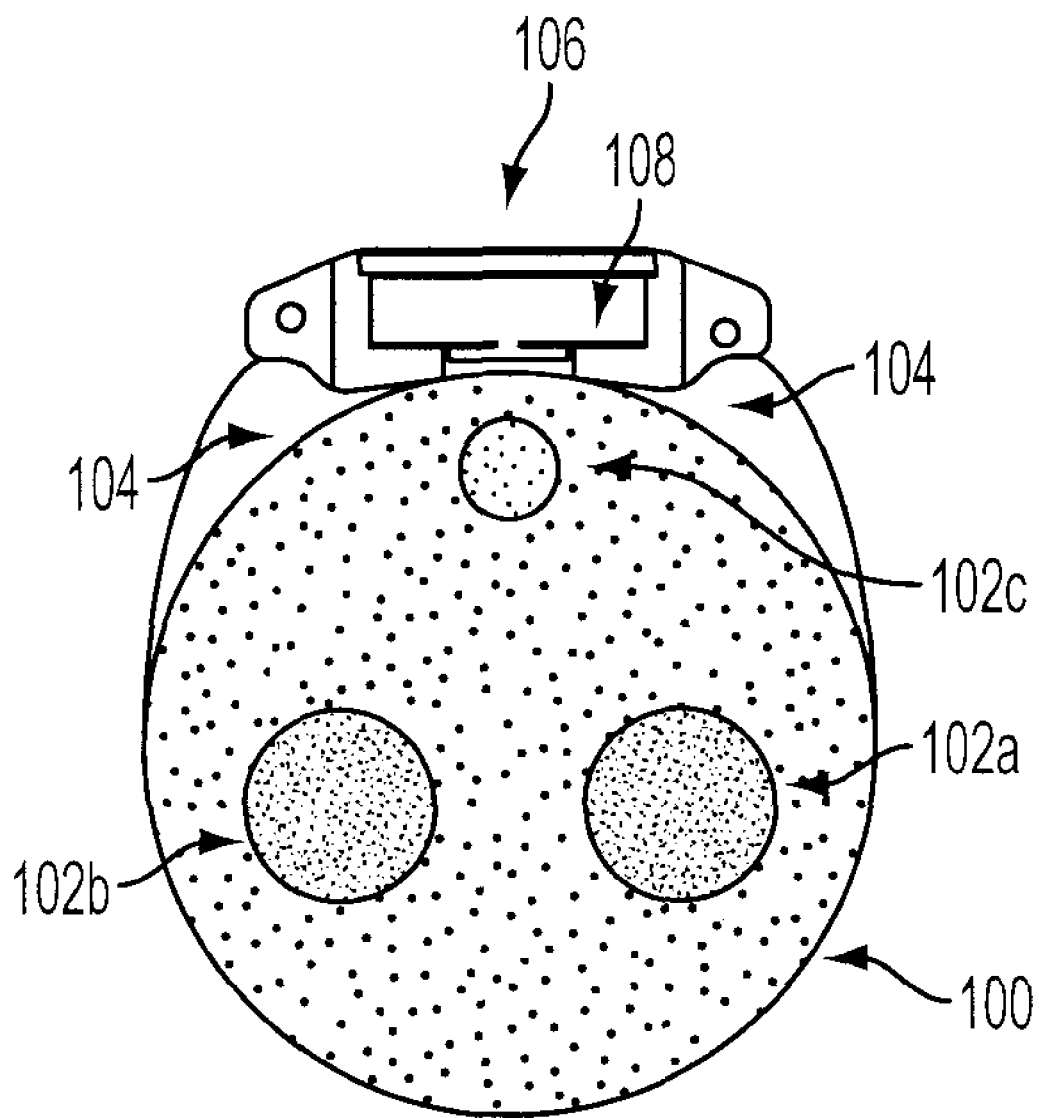
FIG. 1 is a diagrammatic representation of an embodiment of an extravasation detection device attached to a patient at or near an injection site.
Figure 5:
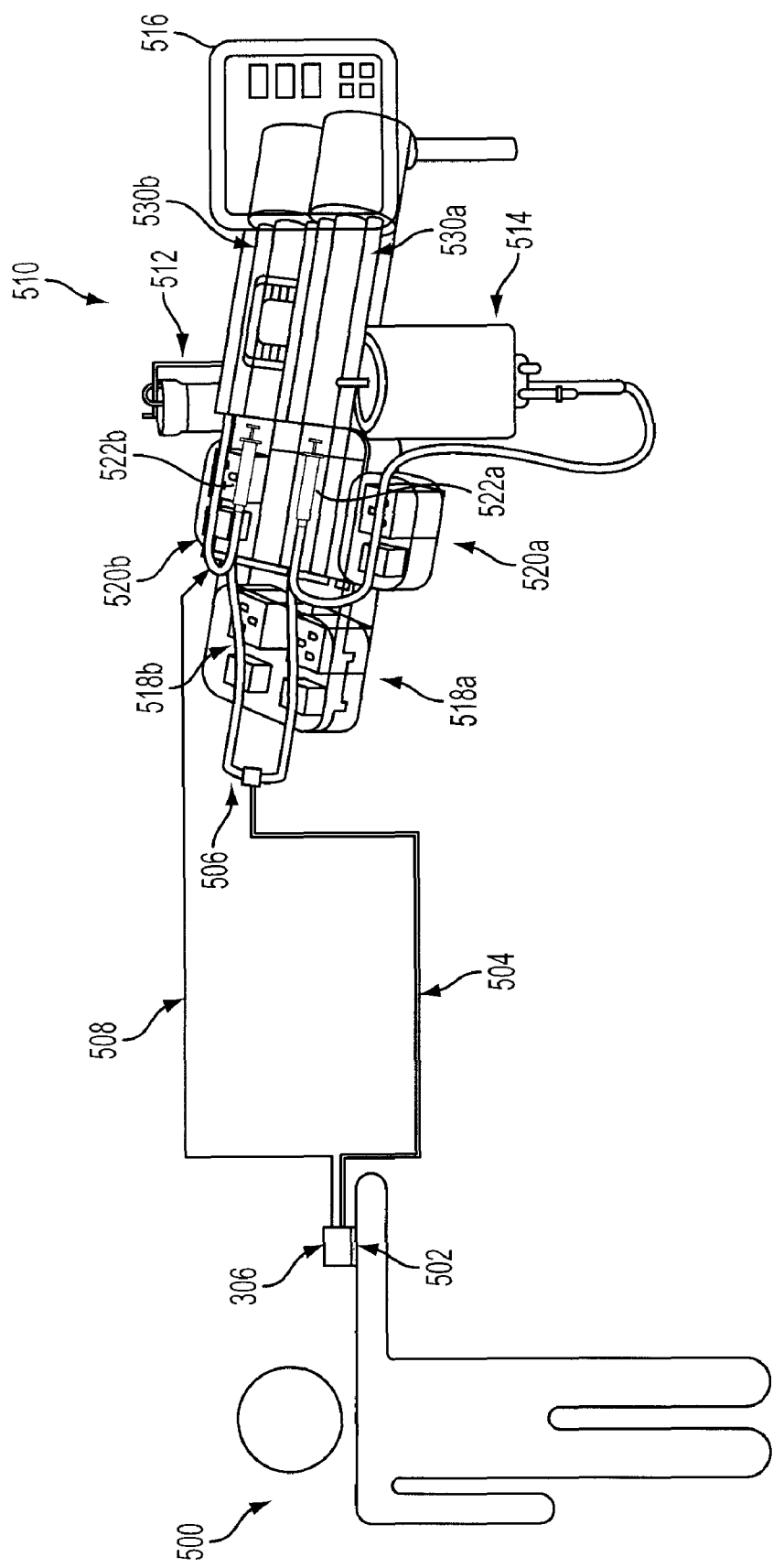
FIG. 5 is a diagrammatic representation of an embodiment of an extravasation detection device that may be used with an automated, or powered, injection system.

FIG. 1 is a diagrammatic representation of an embodiment of an extravasation detection device (EDD) 106 attached to a patient at or near an injection site. For example, the EDD 106 may be attached to a patient's arm or hand, near a blood vessel into which an injection of a medical fluid, such as contrast media, is to take place. FIG. 1 includes a cross-sectional view of a patient's arm or hand 100. Various blood vessels (e.g., veins) 102a, 102b, 102c are also shown. One object of the EDD 106 is to detect extravasation that may occur for small injections of contrast media (e.g., 10 mL or less) to prevent injuries to the patient at a very early stage. The EDD 106 shown in FIG. 1 is transducer (e.g., load-cell or pressure-sensor) based and is placed over or near the injection site of the patient. If the contrast medium begins leaking (e.g., out of one of the patient's veins and into the skin tissue), thereby causing extravasation, a blister may form and press against the transducer 108. In one embodiment, the transducer 108 may comprise a load cell or pressure sensor. The transducer 108 senses the force or pressure applied against it and may then generate a corresponding signal, such as an electrical signal, that is representative of the sensed force or pressure. The electrical signal, such as a voltage signal, may be transmitted by the transducer 108 to an external device that may then provide a warning or alarm to a physician or operator indicating that potential extravasation has been detected. If the EDD 106 is coupled to an automated injection system (such as is shown in FIG. 5), the injection system may use received signals from the EDD 106 to trigger a shutdown operation of the injector to avoid further potential extravasation of fluid from the patient.

In one embodiment, the EDD 106 includes a disposable enclosure, or cover. This cover may be made of a soft, flexible or an elastomeric material, such as plastic, latex, vinyl, or other material. In one embodiment, a physician may strap the EDD 106 to the patient near the injection site. The strap 104 is used to securely attach the EDD 106 to the patient. In another embodiment, the physician may alternatively attach the EDD 106 to the patient using removable adhesive that is applied to the enclosure (cover) of the EDD 106. The strap 104 or removable adhesive (not shown in the embodiment of FIG. 1), along with the corresponding enclosure, may be used on a per-patient basis and disposed of after each individual procedure. The remainder of the EDD 106, however, including the transducer 108, may be reused from one patient to the next.

The EDD 106 shown in FIG. 1 may provide various benefits and advantages. For example, a sensitive load cell used in the EDD 106 may generate signals that may be quickly processed to detect potential extravasation at very early or initial stages, which may help prevent injuries to the patient. The EDD 106 is also easy to use, and various components are reusable (such as the transducer 108, along with the EDD housing). The disposable components are those that come into contact with the patient, such as the enclosure and the corresponding strap 104 or adhesive.

Figure 2A:
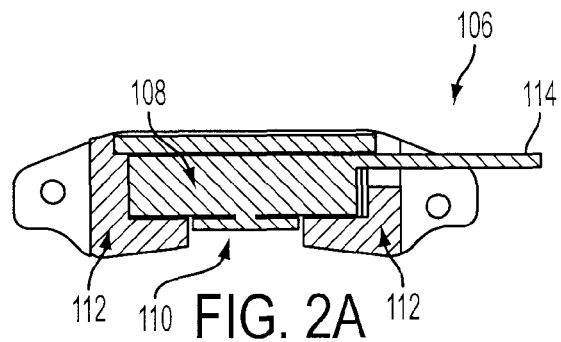
FIG. 2A-2C and FIG. 3A-3B are diagrams of various views of certain embodiments of an extravasation detection device.
Figure 2B:
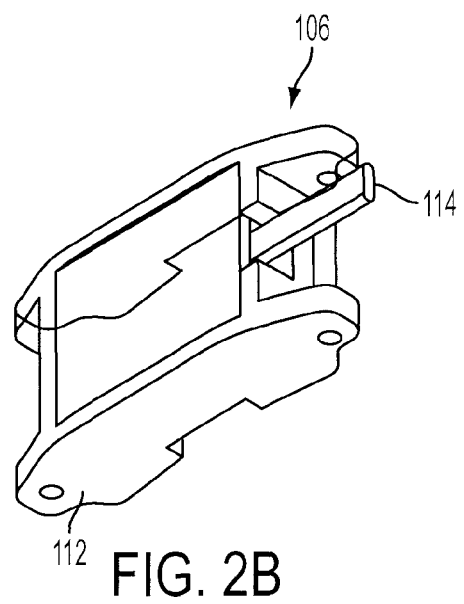
Figure 2C:
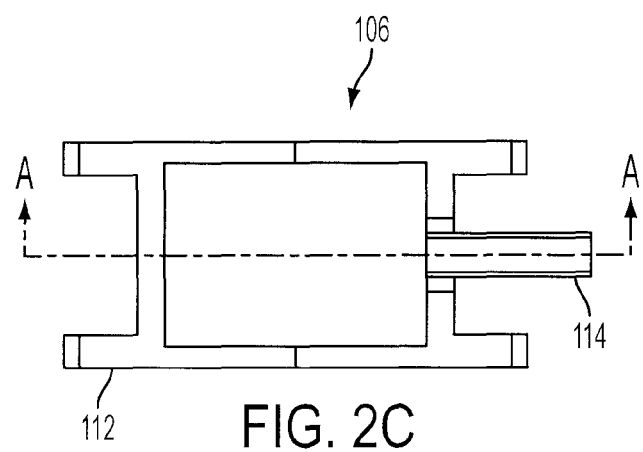
Figure 3A:
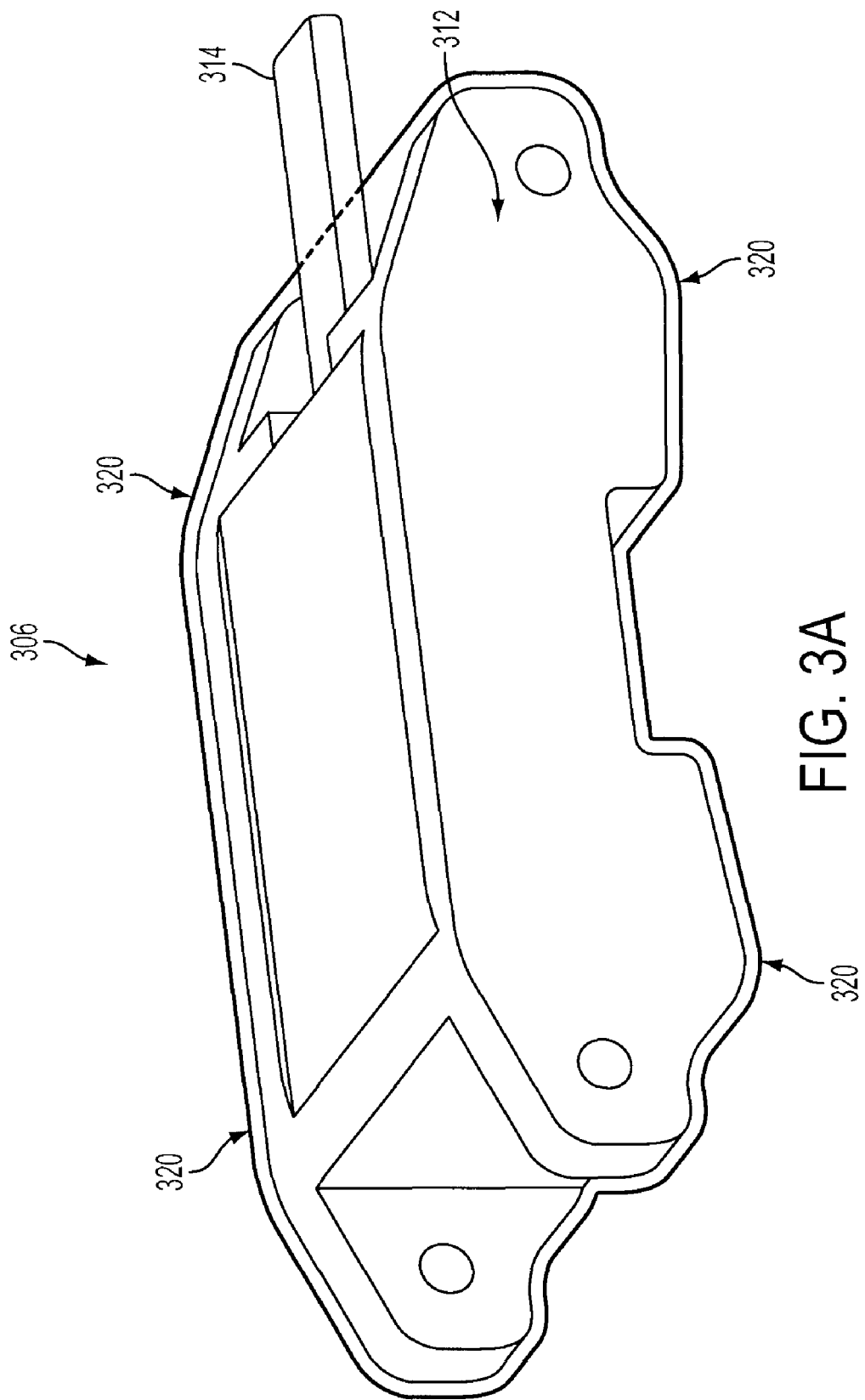

FIG. 2A-2C and FIG. 3A-3B are diagrams of various views of certain embodiments of the extravasation detection device (EDD) 106. FIG. 2A shows a side, sectional view of one embodiment of the EDD 106. The transducer 108 (e.g., force or pressure sensor) of the EDD 106 is included within a sensor housing 112. The bottom portion of the transducer is coupled with a load platen 110. The bottom portion of the EDD 106 is placed upon a surface of a patient's skin near an injection site, as indicated in FIG. 2A. A lead 114 that is shown in FIG. 2A is capable of transmitting signals that are generated by the EDD 106 to a remote device, such as a detection interface or an automated injection system. The transmitted signals represent the amount of force or pressure that is detected by the transducer 108 of the EDD 106. FIG. 2A shows the reusable components of the EDD 106. The EDD 106 may also include a disposable enclosure, which is shown in FIG. 3A. The disposable enclosure, which may comprise a flexible or elastomeric enclosure, comes into direct contact with the patient's skin, and may be removed after a patient procedure so that the remainder of the EDD 106 may be reused for additional patient procedures.

FIG. 2B and FIG. 2C show alternate perspective views of the EDD 106. FIG. 2B shows a perspective view of the EDD 106. FIG. 2C shows a top view of the EDD 106. As seen in the figures, FIG. 2A actually shows a sectional view of the EDD 106 from FIG. 2C along line A-A.

In one embodiment, the EDD 106 includes a force sensor, such as a load cell, as the transducer 108. The load cell is encased in the housing 112 (such as a plastic housing) and either a portion or the entire assembly is enclosed in a disposable cover, such as an elastomeric enclosure, for sterility purposes. The EDD 106 is attached to the patient's skin, such as by using a flexible or an elastomeric strap, or by using a removable adhesive. The EDD 106 is placed at or near the injection site where a cannula is placed in a vein of patient. The distance between the sensor load platen 110 and the surface of the patient's skin can be adjusted and varied as desired, to adjust the sensitivity of the EDD 106 and potential response time for detecting an amount of force applied to the EDD 106 by the patient's skin. In some cases, a physician or other technician may also initiate a vein patency test on the patient by injecting an amount of diluent, such as saline. In some embodiments, the EDD 106 may be able to detect extravasation during such a patency test. Even during a successful test, this patency injection may, for certain individuals, cause the vein to bulge somewhat and touch the load platen 110. This amount of bulging can be used as a reference point for these individuals. For example, a system interfacing with the EDD 106 may receive all signals generated by the EDD 106 and transmitted by the EDD lead 114. When a first signal level (e.g., voltage level) is transmitted by the EDD 106 to the interfaced system during a vein patency test, this system may use this first signal level as a reference point. During the actual injection procedure (when contrast agent is being delivered), if the EDD 106 generates and transmits a signal having a value that is greater than the value of the reference signal (or is greater by a predetermined delta amount), the interfacing system may determine that potential extravasation is occurring, and deliver a warning alarm or signal. If part of an automated injection system, the interfacing system may also stop or shut down the injection process to avoid further extravasation of fluid from the patient. In one embodiment, the EDD 106 includes a pressure sensor, such as a pressure transducer, as the transducer 108.

In one embodiment, the EDD 106 is capable of detecting less than five ml of contrast extravasation. The transducer 108 of the EDD 106 may comprise a force or a pressure transducer. If the transducer 108 comprises a force transducer, the sensor may comprise either a compression or tension load cell, according to one embodiment. The housing 112 of the EDD 106 may be any type of hard plastic or metal, according to some embodiments. The disposable enclosure comprises a flexible, soft or elastomeric material that can flex with the skin bulge and help provide a sterile barrier between an individual and the device, according to one embodiment. In some embodiments, the disposable enclosure may be made of a plastic material that provides a sterile barrier. In some embodiments, the disposable enclosure may be made of a flexible material, such as latex or vinyl, that also provides a sterile barrier. In some embodiments, the disposable enclosure is made of a low-cost material, as it may be disposed of after an individual patient use.

FIG. 3A is a perspective view of an extravasation detection device (EDD) 306 that includes a disposable enclosure 320. As shown in the figure, the EDD 306 includes a housing 312 and a lead 314. In one embodiment, the housing 312 is constructed of a plastic material. In other embodiments, other materials may be used, such as metal. The lead 314 is capable of transmitting electronic signals representative of the detected force or pressure that is applied by the patient's skin to the EDD 306. These signals may be transmitted by the lead 314 to an external system, such as a powered injection system, for processing. In one embodiment, the lead 314 includes an insulating cover.

The EDD 306 further includes a disposable enclosure 320. The enclosure 320 surrounds and encloses the housing 312 of the EDD 306 in the example shown in FIG. 3A. In one embodiment, the enclosure 320 includes an opening through which the lead 314 may pass. The disposable enclosure 320 may be made of an elastomeric material, or may alternatively be made of another material that provides a sterile boundary between the remainder of the EDD 306 and the patient. The enclosure 320 snugly fits around the housing 312 of the EDD 306 and is made of a material such that the force or pressure applied against the EDD 306 may be readily and accurately detected by the sensor. The disposable enclosure 320 may be used on a per-patient basis, and therefore may be disposed of after an individual patient procedure has completed. The remainder of the EDD 306, including the housing 312, lead 314, and sensor (not shown in FIG. 3A), may be reused for various different patient procedures. Therefore, the embodiment of the EDD 306 shown in FIG. 3A includes multi-use components and a single-use component.

The EDD 306 may further include a flexible or elastomeric strap, or an adhesive coating, that is attached to the disposable enclosure 320. The strap or adhesive may be used to attach the EDD 306 to a patient. In one embodiment, the strap or adhesive is disposable and may be used on a per-patient basis.

Figure 3B:
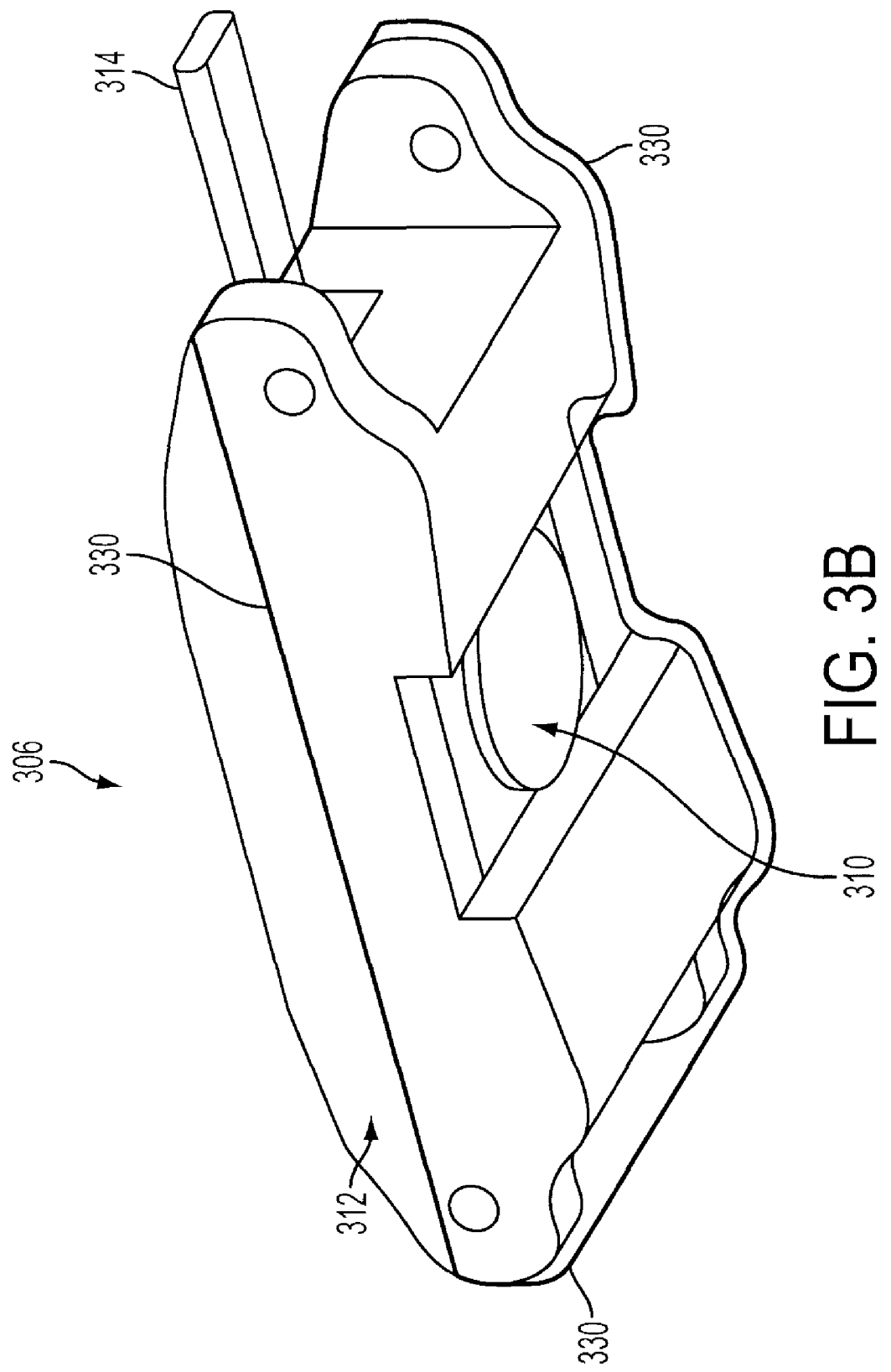

FIG. 3B shows a perspective view of an alternate embodiment of the EDD 306, wherein a disposable enclosure 330 covers only a portion of the EDD housing 312. As shown in the figure, the enclosure 330 covers the bottom portion of the EDD 306, including the transducer (sensor) 310 on the bottom portion of the housing 312. The enclosure 330 may be made of a flexible or elastomeric material and can therefore be fitted around a portion of the EDD 306. In the embodiment shown in FIG. 3B, the enclosure 330 covers only that portion of the EDD 306 that would otherwise substantially come into contact with the patient's skin. The enclosure 330 is made of a material that provides a sterile barrier between the patient and EDD 306, and may be used on a per-patient basis. As such, the enclosure 330 may be disposed of after an individual patient procedure. The remainder of the EDD 306, including the housing 312 and the lead 314, may be reused over multiple patient procedures.

Figure 4:
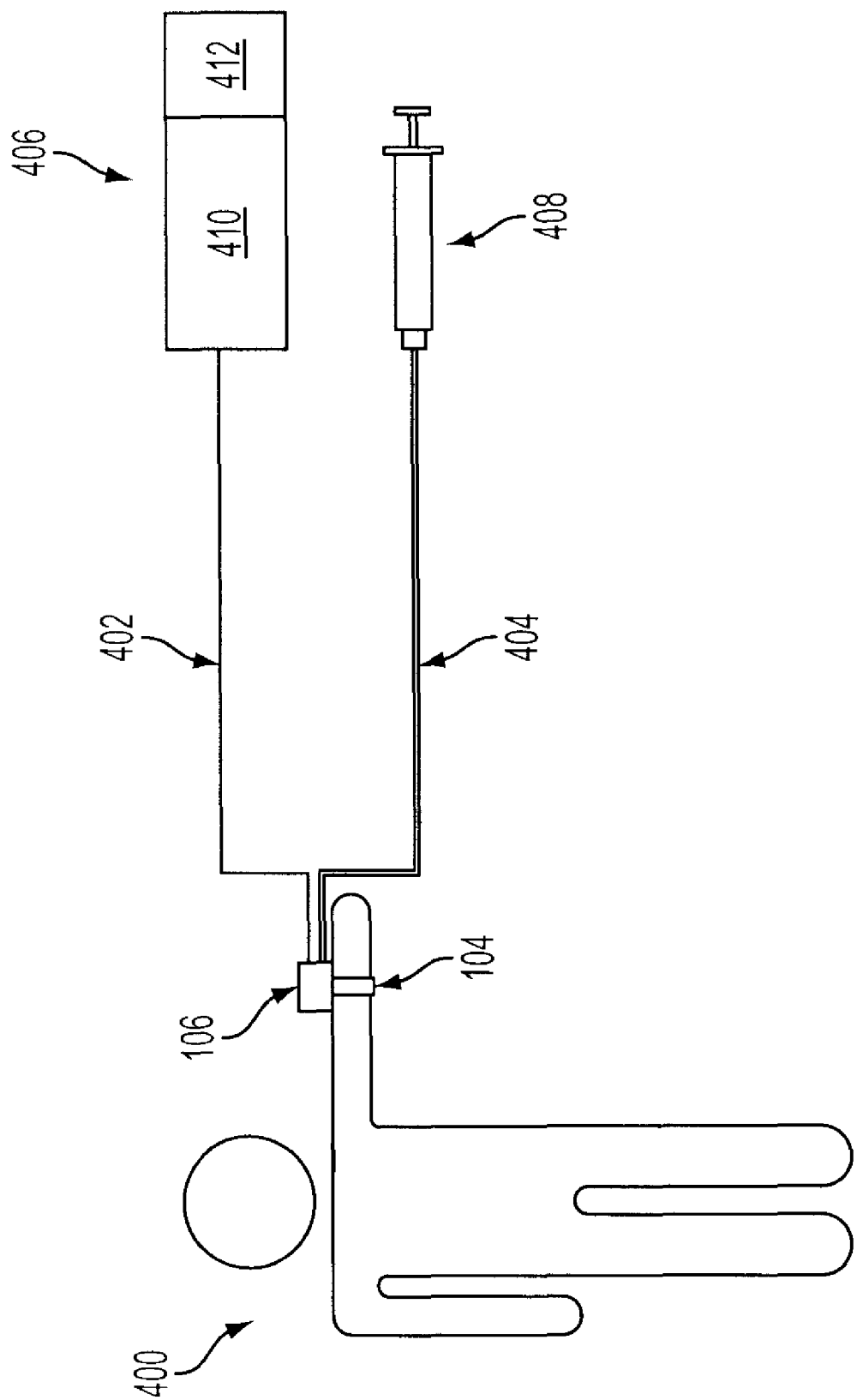
FIG. 4 is a diagrammatic representation of an embodiment of an extravasation detection device that may be used with a manually operated syringe for injection of contrast media into a patient.

FIG. 4 is a diagrammatic representation of an embodiment of an extravasation detection device (EDD) that may be used with a manually operated syringe for injection of medical fluid, such as contrast media, into a patient 400. As shown in the example of FIG. 4, the EDD 106 is used, although the EDD 306 may also be used in other embodiments. The EDD 106 is attached to the patient 400 using a strap 104, such as a flexible or elastomeric strap. The EDD 106 includes a lead 402 that is coupled to an external system 406 comprising an extravasation detector interface 410 and a user interface 412. The EDD 106 is placed upon the patient 400 in close proximity to the injection site of medical fluid, such as contrast media. The syringe 408 injects such fluid into the patient 400 by way of tubing 404 that is coupled to the syringe 408. A clinician manually operates the syringe 408 to inject fluid into the patient 400, according to one embodiment. The fluid travels through the tubing 404 that is shown and is injected into the patient 400 via a cannula.

As described above, the EDD 106 is capable of detecting force or pressure that is applied by the patient's skin against the sensor of the EDD 106. For example, the force or pressure of a blister that may begin to form due to extravasation can be sensed by the EDD 106. The EDD 106 is capable of detecting any other forms of force or pressure that may be applied and that are caused for skin bulges, deformations, or other shaping characteristics. Signals representative of detected forces or pressures are generated by the EDD 106 and transmitted to the external system 406 via the EDD lead 402.

As shown in the example of FIG. 4, the external system 406 includes an extravasation detector interface 410 and a user interface 412. The external system 406 is capable of providing warning signals or alarms to the operator of the manual syringe 408 to indicate the event of extravasation (or potential extravasation). The detector interface 410 processes the incoming signals generated by the EDD 106. Based on the configuration or rules set up on the external system 406, the detector interface 410 will determine when a potential extravasation event has occurred in the patient 400. This will typically occur when the sensed signal (e.g., voltage), which is representative of a force or pressure applied by the patient's skin against the EDD 106, reaches or exceeds a configured or predetermined value. This value may be based on various factors, including patient characteristics or history of extravasation, the type of procedure or timing of fluid injection, the injection location (e.g., hand or arm), and results from vein patency tests. The configured or predetermined threshold values can be pre-loaded or configured on the external system 406, but can be adjusted by a trained clinician, according to one embodiment, to account for physician-, patient-, or other procedure-specific considerations.

If the detection interface 410 has determined that an extravasation (or potential extravasation event) has occurred, it can cause the user interface 412 to generate an alarm for the operator of the syringe-based injection. For example, the user interface 412 could initiate a visible alarm on a graphical display, or could also initiate an audible alarm via coupled speakers, so that the operator could take appropriate action. For example, once the operator perceives the alarm, he or she could decide to stop the injection or to abort the patient procedure in order to avoid injuring the patient 400.

FIG. 5 is a diagrammatic representation of an embodiment of an extravasation detection device (EDD) that may be used with an automated, or powered, injection system 510. In alternate embodiments, other forms of powered or automated injectors may be used. In this embodiment, the EDD is the EDD 306, although the EDD 106 may be used in other embodiments. The EDD 306 is attached to a patient 500 (in proximity to the injection site), such as by use of a strap or adhesive 502. The injection system 510 includes a user interface 516, a container of medical injection fluid (such as contrast media) 512, a container of diluent (e.g., saline) 514, an injection pump 522b for contrast media, an injection pump 522a for diluent, motor/actuator units 530a and 530b, and associated tubing from the containers 512 and 514 to the respective pumps 522b and 522a. In the embodiment shown in FIG. 5, the pumps 522b and 522a comprise syringes. In other embodiments, other forms of pumps may be used, such as peristaltic pumps. In other embodiments, a single pump may be used for both contrast and saline. The tubing passes through assemblies 520b and 520a. In the example of FIG. 5, the assemblies 520b and 520a include pinch-valve and air-detect components. The pinch-valve components are controlled by the system 510 to selectively allow or restrict fluid flow from the containers 512 and 514 to the pumps 522b and 522a, respectively. The air-detect components are capable of generating signals upon detection of air bubbles or air columns within the tubing lines, such signals being propagated to and processed by the system 510. In other embodiments, other types of valves may be used to selectively allow or restrict fluid flow. In some embodiments, the system 510 does not include air-detect components. In certain embodiments, air-detect components are not used, but other forms of air-prevention or air-removal mechanisms may be in place for the system 510.

Output tubing leads away from the pumps 522b and 522a to a Y-connector 506 and towards tubing 504 that leads to the patient 500 for injection of medical fluid. The Y-connector 506 further includes a valve, such as a check valve or other mechanism, to permit fluid flow towards the patient 500 but prohibit fluid flow back from the patient 500 towards the system 510, according to one embodiment. In the embodiment shown in FIG. 5, the pumps 522b and 522a comprise dual-port syringes that each have an input port (for input tubing) and an output port (for output tubing). The output tubing from the pumps 522b and 522a flow to the Y-connector 506 through additional pinch-valve and air-detect components (in assemblies 518b and 518a), which control the flow of output fluid to the patient 500 and monitor the lines for air bubbles or air columns.

The injection system 510 of FIG. 5 includes a detector interface that processes the incoming signals generated by the EDD 306 and transmitted by the lead 508 to the system 510. This detector interface may be incorporated into the injection system 510. Similar to the external system of FIG. 4, the injection system 510 of FIG. 5 is capable of determining when an extravasation event (or potential extravasation event) is taking place. When this determination has been made, the injection system 510 may also initiate a visible or audible alarm using the user interface 516 to alert the operator of the event. In addition, the injection system 510 is also capable of automatically halting or terminating an injection procedure to avoid injuring the patient 500.

Figure 6A:
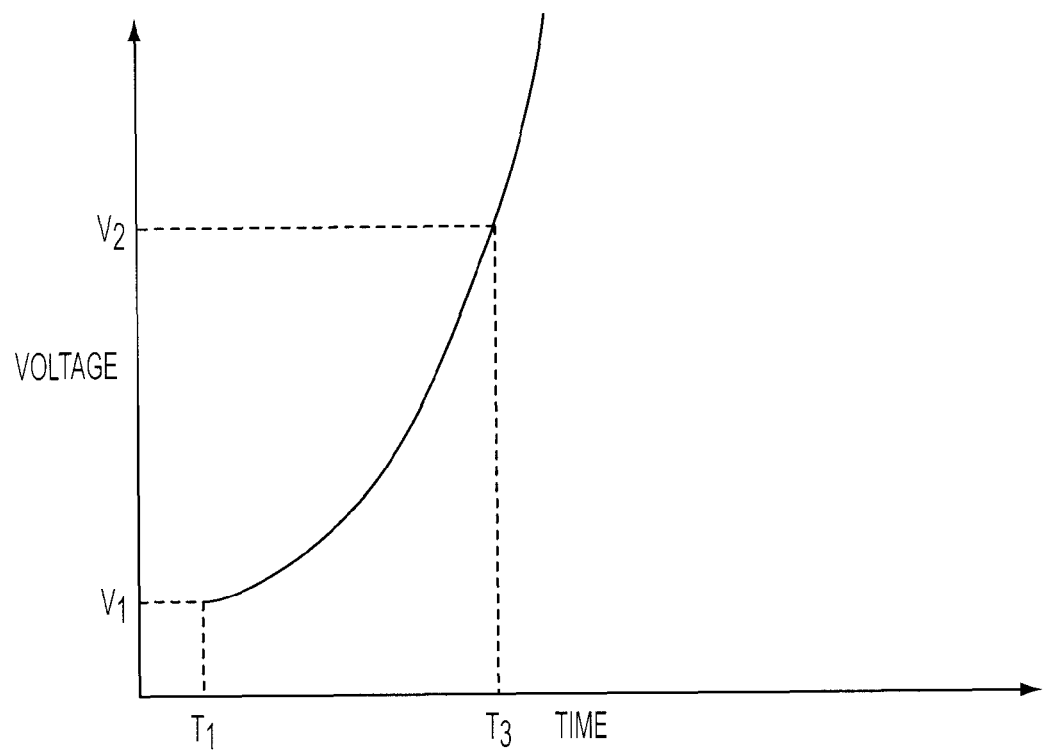
FIG. 6A-6B are diagrams of exemplary graphs showing voltage generated by the extravasation detection device as a function of time.
Figure 6B:
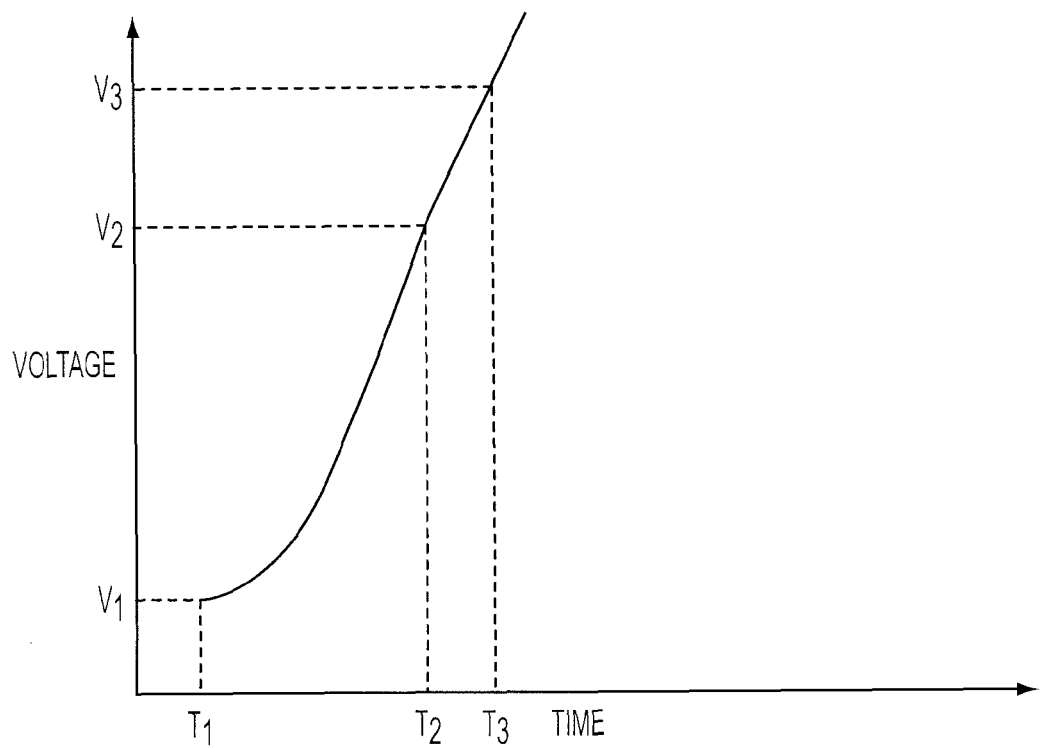

FIG. 6A-6B are diagrams of exemplary graphs showing voltage generated by the extravasation detection device (EDD) as a function of time. These voltage signals may be generated by any of the EDD embodiments described above, such as the EDD 106 or EDD 306. As force or pressure is applied by a patient's skin against the EDD, the EDD generates a signal representative of the sensed force or pressure. Over time, and during individual patient procedures, the EDD generates a set of signals that are transmitted to an external system across the lead (as shown in prior figures).

FIG. 6A shows a first exemplary graph of voltage generated by the EDD as a function of time. At the initial stage of an individual patient injection, the EDD generates a voltage $V_1$ (which may, in certain scenarios, be zero or substantially zero). Over time, the EDD regularly generates increased voltage levels due to increased force or pressure applied by the patient's skin against the EDD. At a particular point, the EDD generates a voltage $V_2$ at a time $T_3$, where $V_2$ is greater than $V_1$. In one embodiment, an external system may determine that voltage level $V_2$ represents an extravasation event and take appropriate action (such as providing a warning signal or terminating the injection procedure).

FIG. 6B shows a second exemplary graph of voltage generated by the EDD as a function of time. As shown in this figure, the generated voltage level increases much more rapidly. An external system may determine that a significant and rapid extravasation event is occurring based upon an interpretation of the voltage signals received from the EDD. In one scenario, the system may issue a warning to the user when it has detected a voltage level $V_2$ transmitted from the EDD at a time $T_2$. In the example of FIG. 6B, the EDD generates the voltage level $V_2$ more quickly than it does in the example of FIG. 6A. The system may issue a further warning and additionally shutdown, or terminate, an injection procedure when it has detected a voltage level $V_3$ transmitted from the EDD at a time $T_3$. In other scenarios, the system may issue warnings and shutdown signals based on preconfigured or specified voltage levels that are lower or higher than $V_2$ and $V_3$, based on physician-, patient-, or other procedure-specific considerations. In some embodiments, the system may issue warnings or shutdown signals based upon how quickly voltage levels change (e.g., delta Voltage/delta Time). In some embodiments, predetermined voltage threshold levels (e.g., $V_2$ or $V_3$) may be based upon prior information, such as information from a vein patency test that was performed on a patient prior to injection of medical fluid.

In one embodiment of the EDD, tests were performed to track generated voltages of the EDD based upon extravasation of fluid. These tests also tracked the amount of pressure detected by the sensor of the EDD. In this test embodiment, the EDD included a load cell (FS20 1500 Grams Force MSI Sensor). Sample test results are shown in Table 1 below. As can be seen from the table, the EDD is capable of detecting small amounts of pressure applied against the sensor for small volumes of extravasation. The EDD is further capable of generating voltage signals that can be effectively processed by an external system, such as an automated injection system. In addition, small variations in volumes of extravasation result is significant changes in generated voltage output, meaning that the external system is capable of detecting extravasation early and quickly to minimize the chance of patient injury.

TABLE 1

| Volume of extravasation (ml) | Sensed Pressure (psi) | Load (volts) |
| --- | --- | --- |
| 0.5 | 2.6 | 2.6 |
| 1 | 3.4 | 7.1 |
| 2 | 4.6 | 14.6 |

Figure 7:
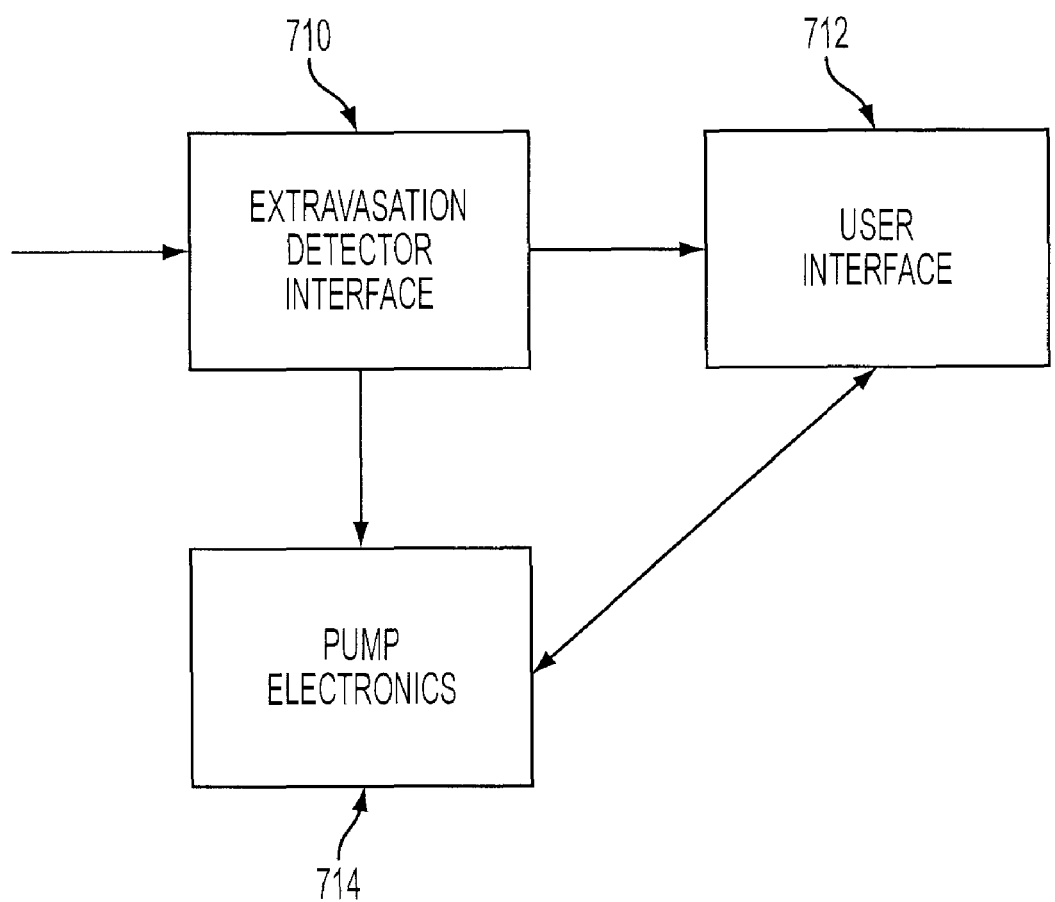
FIG. 7 is a diagram of components that may be incorporated into an automated injection system that is coupled to an extravasation detection device, according to one embodiment.

FIG. 7 is a diagram of components that may be incorporated into an automated injection system that is coupled to an extravasation detection device (EDD). For example, these components may be incorporated into the automated injection system 510 shown in FIG. 5. The automated injection system is coupled to the EDD via the lead, which is capable of transmitting electrical signals that are generated by the EDD.

As shown in FIG. 7, the automated injection system includes an extravasation detector interface 710. This detector interface 710 may provide functions similar to the detector interface 410 shown in the external system on FIG. 4, according to one embodiment. In one embodiment, the detector interface 710 receives and processes the incoming signals generated by the EDD to determine if an extravasation event, or a potential extravasation event, is occurring in the patient. If the detector interface 710 determines that such an event has occurred, it may communicate with the pump electronics 714 and/or the user interface 712. For example, the detector interface 710 may communicate with the user interface 712 to cause a warning message (e.g., visible message, audible message) to be provided to the operator of the system. In one embodiment, the user interface 712 may provide options to the user, such as injection options, when an event has been generated by the detector interface 710. By selecting one of these options, the operator may be able to terminate the injection, pause the injection, or change injection parameters to minimize the possibility of patient injury that may be caused by extravasation of fluid.

The detector interface 710 may also communicate with the pump electronics 714 of the injection system to terminate or pause an injection procedure automatically upon detection of an extravasation event. The status of the pump electronics 714 may be displayed on the user interface 712.

Various embodiments of an extravasation detection device (EDD) have been described above and are shown in the accompanying figures. These and other embodiments may be used during different types of medical procedures in which a medical fluid is injected into a patient's vascular system. For example, various embodiments of the EDD may be used during a computed tomography (CT) procedure. In addition, various embodiments of the EDD may potentially be used for CT angiographic procedures or magnetic resonance imaging (MRI) procedures. Certain embodiments may be used to detect extravasation of any form of medical fluid during an injection procedure to help prevent injury to a patient.

The foregoing description addresses embodiments encompassing the principles of various embodiments the present invention. The embodiments may be changed, modified and/or implemented using various types of arrangements. Those skilled in the art will readily recognize various modifications and changes that may be made to these embodiments of the invention without strictly following the exemplary embodiments and applications illustrated and described herein, and without departing from the scope of the invention, which is set forth in the following claims.

What is claimed is:

1. An extravasation detection device, comprising:
an enclosure;
an attachment coupled to the enclosure to be removably connected to a patient; and
a detection assembly at least partially enclosed within the enclosure, the detection assembly comprising:
  a housing; and
  a transducer coupled to the housing to generate a signal representative of a force or pressure applied to the transducer caused by extravasation of medical fluid from the patient;
wherein the detection assembly, when operable, provides adjustment of a distance between the transducer and the patient to correspondingly adjust a sensitivity of the device in detecting extravasation of medical fluid from the patient.

2. The extravasation detection device of claim 1, wherein:
the enclosure comprises a disposable enclosure;
the attachment comprises a disposable attachment; and
the detection assembly comprises a reusable detection assembly.

3. The extravasation detection device of claim 2, wherein the disposable enclosure and the disposable attachment are usable on a per-patient basis.

4. The extravasation detection device of claim 2, wherein the disposable enclosure comprises a sterile enclosure.

5. The extravasation detection device of claim 1, wherein the enclosure is constructed of an elastomeric material.

6. The extravasation detection device of claim 1, wherein the attachment comprises a flexible strap.

7. The extravasation detection device of claim 1, wherein the transducer comprises a force or pressure sensor.

8. The extravasation detection device of claim 1, wherein the housing of the detection assembly is constructed of a plastic material.

9. The extravasation detection device of claim 1, further comprising a lead to transmit the generated signal to an external device.

10. The extravasation detection device of claim 1, wherein the device is operable to transmit the generated signal to an external device.

11. The extravasation detection device of claim 1, wherein the detection assembly is fully enclosed within the enclosure.

12. A system, comprising:
an injector device; and
an extravasation detection device, comprising:
  an enclosure;
  an attachment coupled to the enclosure to be removably connected to a patient; and
  a detection assembly at least partially enclosed within the enclosure, the detection assembly comprising a housing and a transducer coupled to the housing to generate a signal representative of a force or pressure applied to the transducer caused by extravasation of medical fluid from the patient, wherein the detection assembly, when operable, provides adjustment of a distance between the transducer and the patient to correspondingly adjust a sensitivity of the extravasation detection device in detecting extravasation of medical fluid from the patient.

13. The system of claim 12, wherein the injector device comprises:
an extravasation detection interface to process signals generated by the transducer of the extravasation detection device; and
a user interface to communicate with the extravasation detection interface.

14. The system of claim 13, wherein the extravasation detection interface causes the user interface to generate a visible or audible alarm when the extravasation detection device has detected an extravasation event.

15. The system of claim 13, further comprises a pump electronics component, wherein the extravasation detection interface causes the pump electronics component to terminate an injection procedure when the extravasation detection device has detected an extravasation event.

16. The system of claim 13, wherein:
the extravasation detection interface causes the user interface to generate a visible or audible alarm when the extravasation detection device has detected a signal exceeding a first threshold level from the transducer of the extravasation detection device; and
the extravasation detection interfaces causes the injector device to terminate an injection procedure when the extravasation detection device has detected a signal exceeding a second threshold level from the transducer of the extravasation detection device, the second threshold level being greater than the first threshold level.

17. The system of claim 13, wherein the injector device causes an alarm or a shutdown event to be generated when the signal generated by the transducer of the extravasation detection device exceeds a predetermined threshold.

18. An extravasation detection device, comprising:
means for enclosing at least a portion of the device, the enclosing means being removable from the device;
means for attaching the device to a patient, the attachment means being coupled to the enclosing means; and
means for detecting extravasation of medical fluid from the patient, the detection means being operable to (i) adjust a distance between the device and the patient to correspondingly adjust a sensitivity of the device in detecting extravasation of medical fluid from the patient and (ii) generate a signal representative of an applied force or pressure caused by extravasation of medical fluid.

* * * * *